(12) United States Patent
Scheker

(10) Patent No.: US 7,708,781 B2
(45) Date of Patent: May 4, 2010

(54) LATERAL ELBOW PROSTHESIS—PROXIMAL RADIOULNAR JOINT

(75) Inventor: Luis Roman Scheker, Glenview, KY (US)

(73) Assignee: Aptis Medical, LLC, Louisville, KY (US)

( * ) Notice: Subject to any disclaimer, the term of this patent is extended or adjusted under 35 U.S.C. 154(b) by 763 days.

(21) Appl. No.: 11/306,312

(22) Filed: Dec. 22, 2005

(65) Prior Publication Data

US 2008/0195217 A1    Aug. 14, 2008

(51) Int. Cl.
*A61F 2/38* (2006.01)
*A61F 2/42* (2006.01)

(52) U.S. Cl. .............. 623/20.11; 623/20.13; 623/21.11; 623/21.13

(58) Field of Classification Search ... 623/20.11–20.13, 623/21.11–21.13, 22.35–22.38, 19.11–19.14
See application file for complete search history.

(56) References Cited

U.S. PATENT DOCUMENTS

| | | |
|---|---|---|
| 3,875,594 A | 4/1975 | Swanson |
| 4,004,300 A * | 1/1977 | English .................. 623/22.17 |
| 4,106,128 A | 8/1978 | Greenwald et al. |
| 4,158,893 A | 6/1979 | Swanson |
| 4,164,793 A | 8/1979 | Swanson |
| 4,178,640 A | 12/1979 | Buechler et al. |
| 4,180,871 A | 1/1980 | Hamas |
| 4,198,713 A | 4/1980 | Swanson |
| 4,229,841 A | 10/1980 | Youm |
| 4,259,752 A * | 4/1981 | Taleisnik ................. 623/21.13 |
| 4,349,922 A | 9/1982 | Agee |
| 4,784,661 A | 11/1988 | Beckenbaugh et al. |
| 5,108,444 A | 4/1992 | Branemark |
| 5,133,762 A | 7/1992 | Branemark |
| 5,314,485 A | 5/1994 | Judet |
| 5,326,364 A | 7/1994 | Clift, Jr. et al. |
| 5,458,646 A | 10/1995 | Giachino et al. |
| 5,507,821 A | 4/1996 | Sennwald et al. |
| 5,702,470 A | 12/1997 | Menon |
| 5,782,926 A | 7/1998 | Lamprecht |
| 5,813,789 A * | 9/1998 | Prickler et al. .............. 403/135 |
| 5,951,604 A | 9/1999 | Scheker |
| 6,059,832 A | 5/2000 | Menon |

(Continued)

FOREIGN PATENT DOCUMENTS

EP    34 192    8/1981

(Continued)

OTHER PUBLICATIONS

Acumed, Acu-Loc Targeted Distal Radius System (Continued)

*Primary Examiner*—Thomas J Sweet
*Assistant Examiner*—Yashita Sharma
(74) *Attorney, Agent, or Firm*—Thersea Fritz Camoriano; Camoriano & Associates

(57) ABSTRACT

A proximal radioulnar joint (lateral elbow) prosthesis includes a radial brace member to be secured to the radius bone and an ulna brace member to be secured to the ulna bone. The radial brace member has a ball at its proximal end, and the ulnar brace member defines a curved cavity which receives and rotationally supports the ball.

8 Claims, 4 Drawing Sheets

U.S. PATENT DOCUMENTS

| | | | |
|---|---|---|---|
| 6,221,073 | B1 | 4/2001 | Weiss et al. |
| 6,306,171 | B1 * | 10/2001 | Conzemius ............... 623/20.11 |
| 6,712,820 | B2 | 3/2004 | Orbay |
| 7,160,331 | B2 * | 1/2007 | Cooney et al. ............ 623/21.11 |
| 2004/0220675 | A1 * | 11/2004 | Lewis et al. ............... 623/20.11 |

FOREIGN PATENT DOCUMENTS

| | | |
|---|---|---|
| FR | 2660856 | 10/1991 |
| GB | 2269752 | 8/1993 |
| WO | 92/00709 | 1/1992 |
| WO | WO 01/01892 A1 | 1/2001 |

OTHER PUBLICATIONS

Hand Innovations, The Anatomical DVR Surgical Technique, from web site.

Kinetikos Medical Incorporated, Universal 2 Total Wrist Implant System, from web site.

Small Bone Innovations, uHead Ulnar Implant System, from web site.

Small Bone Innovations, Total Wrist Implant, from web site.

Stryker, Universal Distal Radius System, from web site.

Wright, Evolve Radial Head Plate, from web site.

CFV Wrist System, Biomet, Inc., Form No. Y-BMT-152/013190.

'Clinical Mechanics of the Hand', Second Edition, 1993 by Mosby-Year Book, Inc., St. Louis, MO.

Silastic HP 100 Swanson Finger Joint Implant and Dow Corning Wright Swanson Finger Joint Grommet II, Dow Coming Wright Catalog.

Sutter Implants for the Hand and Forearm, brochure by Sutter Corporation; 4 pages; dated Feb. 12, 1990.

The Journal of Bone and Joint Surgery, vol. 69-A, No. 7, Sep. 1987, Jayasanker Menon, MD, 'Total Wrist Replacement Using the Modified Volz Prosthesis'.

The Journal of Hand Surgery, vol. 20A No. 1, Hans Christoph Meuli, MD, et al.,. Jan. 1995, "Uncemented Total Wrist Arthroplasty", pp. 115-121, 802.

Mayo Clinic College of Medicine, 200 First Street SW, Rochester, MN 55905; 'Use of an Ulnar Head Endoprosthesis for treatment of an unstable distal ulnar resection: Review of mechanics, indications, and surgical technique.' 2005 Elsevier Inc.

Wright, Locon VLS Distal Radius System, from web site.

* cited by examiner

LATERAL ELBOW PROSTHESIS—PROXIMAL RADIOULNAR JOINT

BACKGROUND

The present invention relates to an elbow or proximal radioulnar joint prosthesis. The elbow joint includes three bones—the humerus, which extends from the shoulder to the elbow, and the radius and ulna, which lie parallel to each other and form the forearm, which extends from the elbow to the wrist. Currently, when the proximal head (the upper end as seen in FIG. 1) of the radius bone is damaged or destroyed, the standard procedure is to excise the damaged portion of the radius and, if deemed necessary, to insert a prosthesis into the radius bone to replace the radial head. This radial head replacement relies on the annular ligament to hold the radius in position as it did prior to the procedure. If this ligament is damaged as part of the incident which caused the damage to the radial head (such as a dislocation or a fracture of the radial head), which is typical, then the prosthesis may become dislocated from the proximal ulna and or humerus and unable to transmit any axial loads from the hand, via the forearm and the elbow, to the humerus. As a result, the patient is not able to transmit axial loads to the radius.

SUMMARY

The present invention provides a proximal radioulnar joint prosthesis that gives the patient a wide range of motion and the ability to bear weight with the affected hand.

DESCRIPTION

Figure 1:
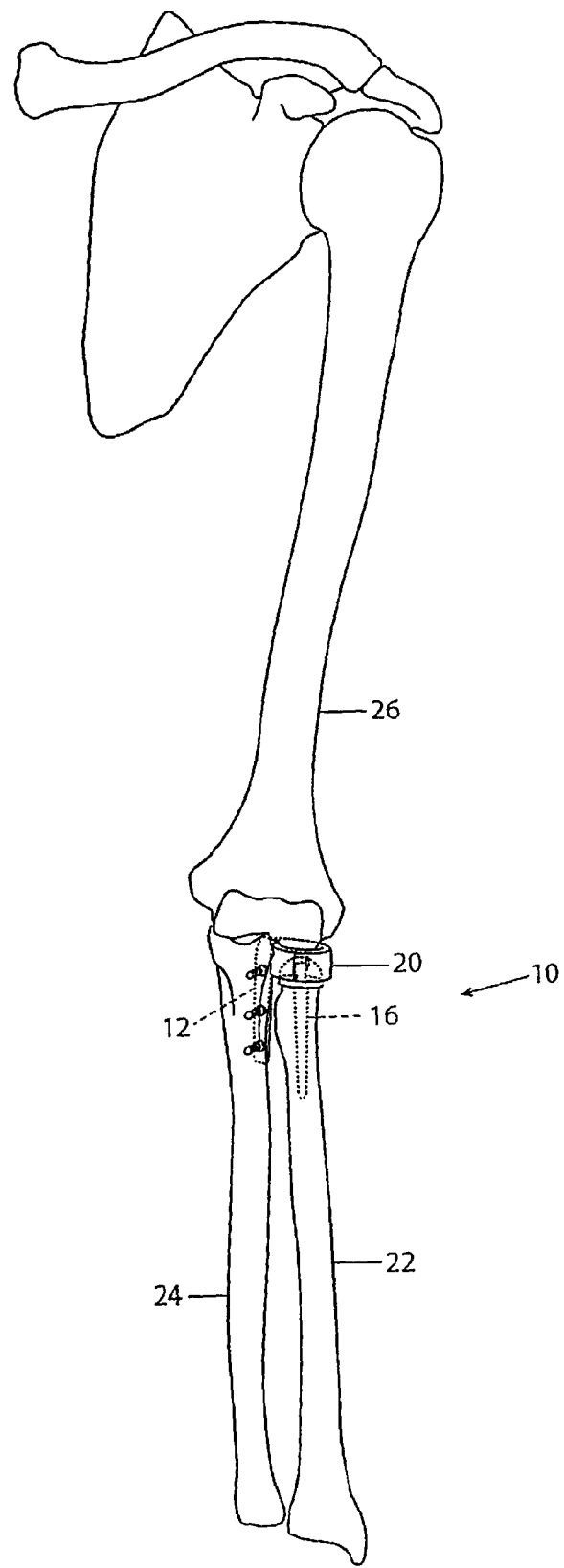
FIG. 1 is a front view of a proximal radioulnar joint prosthesis made in accordance with the present invention, installed on a human skeleton.

FIGS. 1-4 show one embodiment of a proximal radioulnar joint prosthesis 10 made in accordance with the present invention. The proximal radioulnar joint prosthesis 10 includes an ulnar brace member 12, which is secured to the ulna bone 24 with a plurality of screws 14. Also included is a radial brace member 16, which is secured to the radius bone 22. The radial brace member 16 includes a stem rod 46 which secures the radial brace member 16 to the radius bone by being press fit into the medullary cavity 48 of the radius bone 22. In addition to or instead of the press fit, the radial brace member 16 may be cemented, adhered, or secured by other means to the radius bone 22. The radial brace member 16 is essentially a shaft, symmetrical about a central axis. A hemispherical ball 18 is mounted onto the upper or proximal end of the radial brace member 16, and the stem rod 46 extends downwardly from the ball 18. Further details of the radial brace member 16 will be described later.

Figure 2:
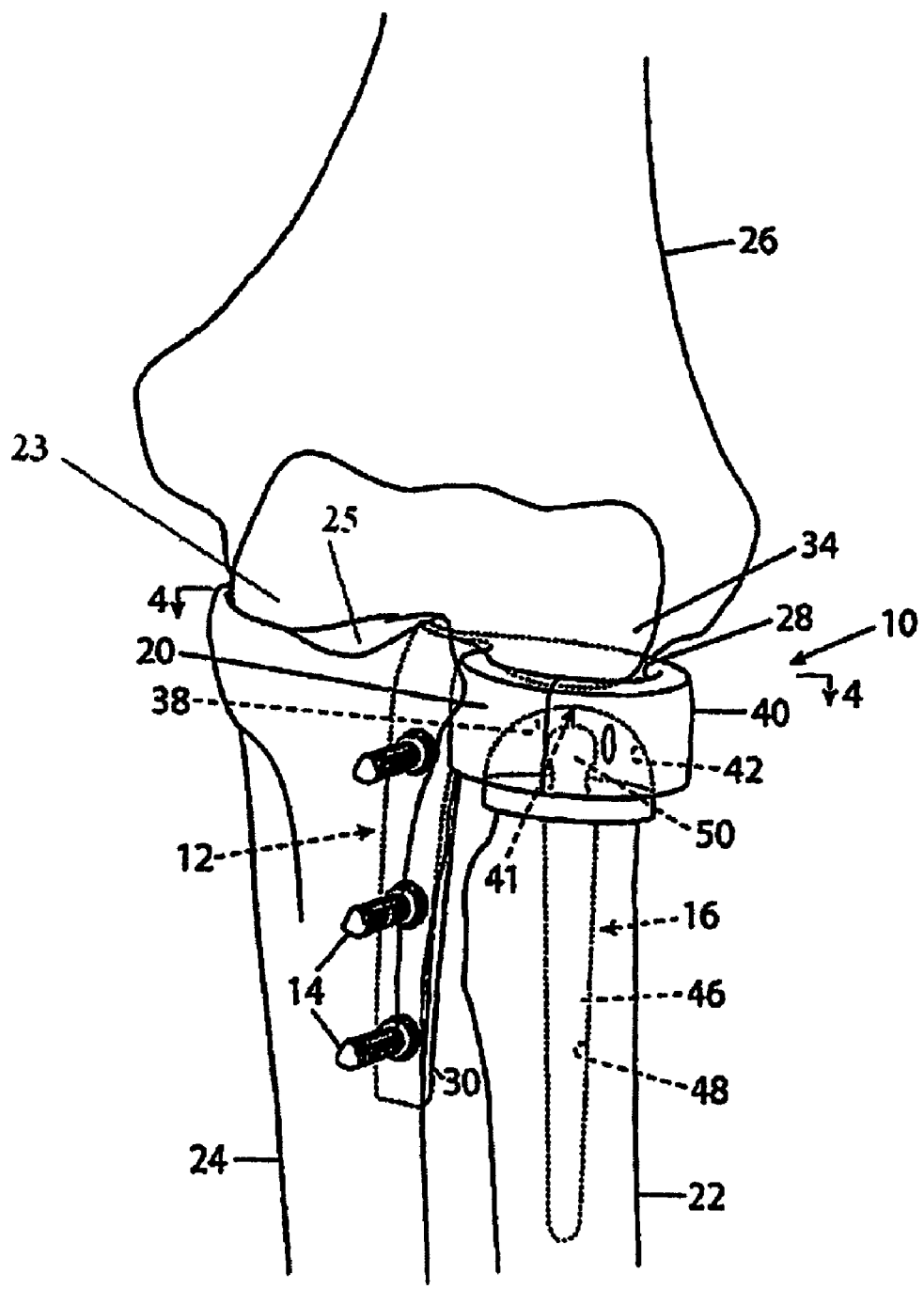
FIG. 2 is an enlarged, broken-away view of the installed proximal radioulnar joint prosthesis of FIG. 1.
Figure 3:
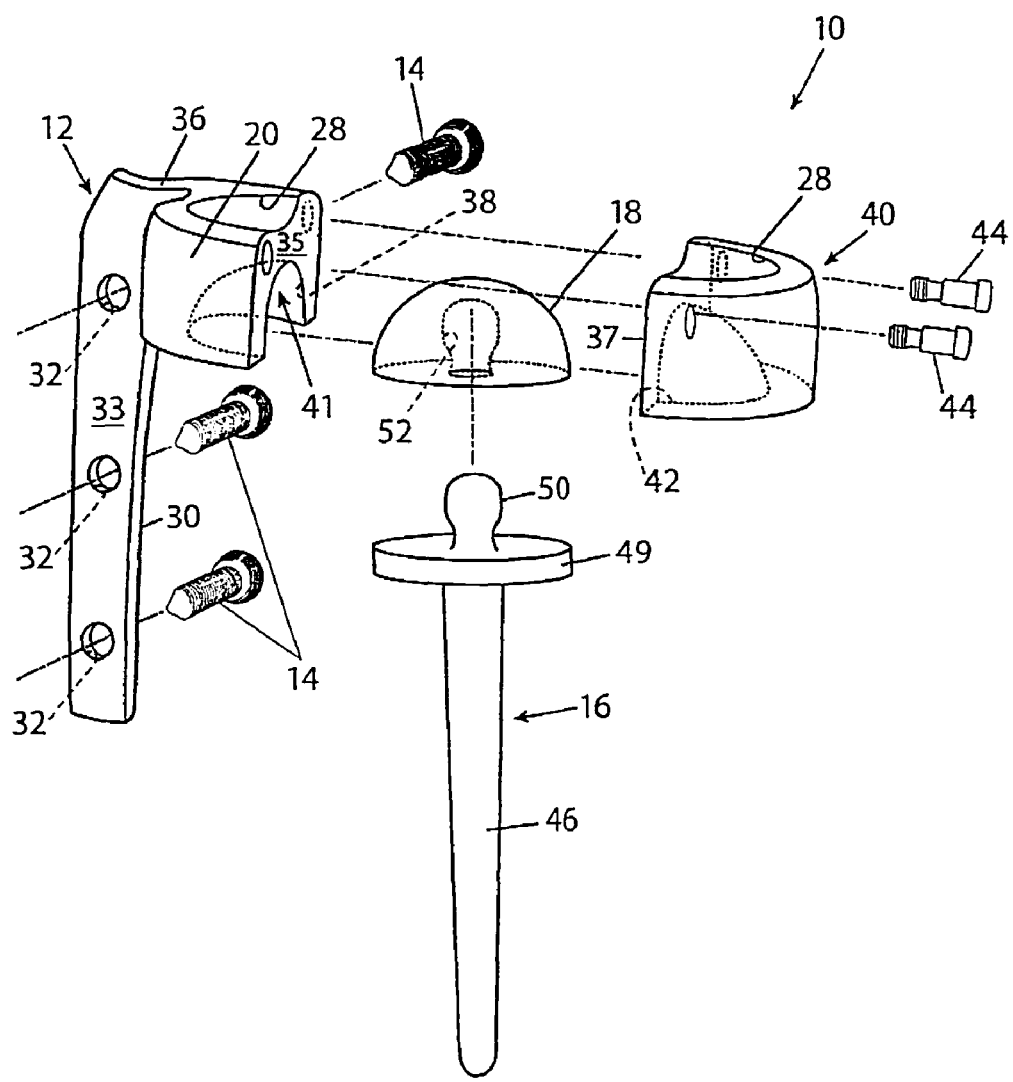
FIG. 3 is an exploded perspective view of the proximal radioulnar joint prosthesis of FIG. 2.
Figure 4:
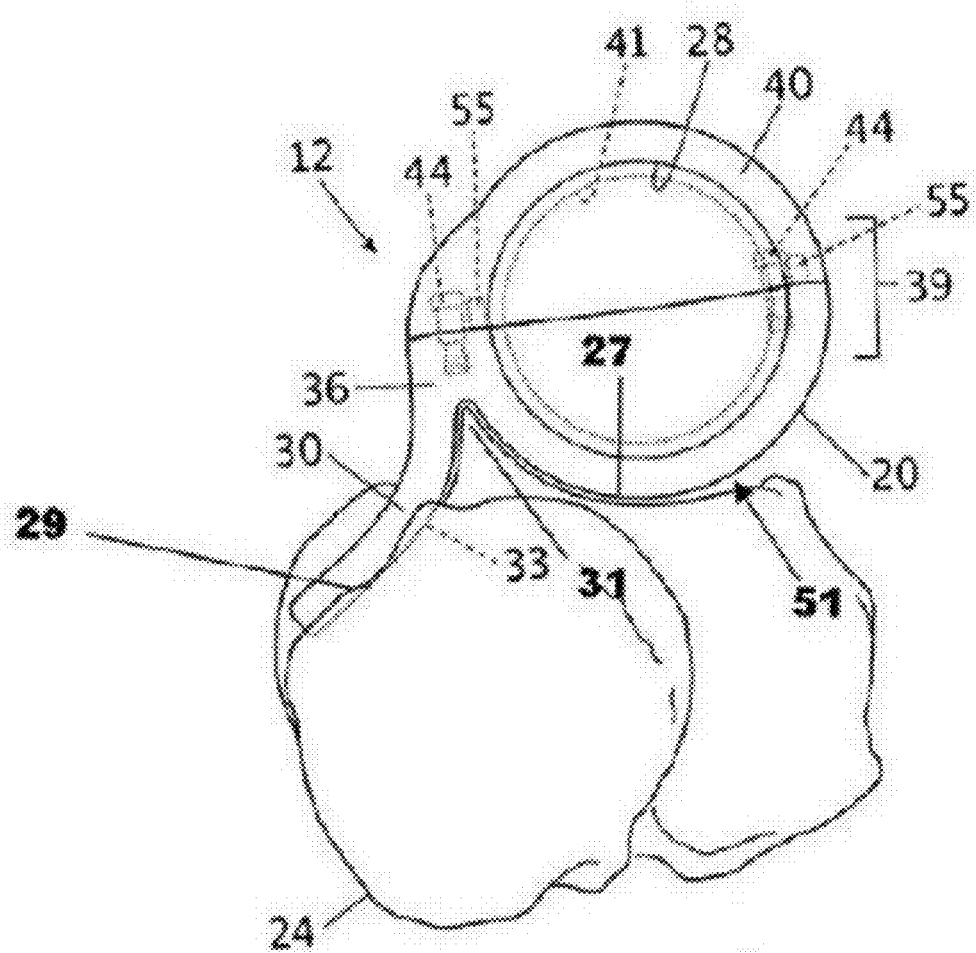
FIG. 4 is a view looking down on the prosthesis along the line 4-4 of FIG. 2.

Referring to FIGS. 2-4, the ulnar brace member 12 includes an elongated portion 30, which lies adjacent to the ulna 24 and which is secured to the ulna 24 by means of screws 14 that extend through openings 32 in the elongated portion 30. The elongated portion 30 is substantially flat and its face 33 that lies adjacent to the ulna 24 is generally shaped to conform to the surface of the ulna 24 in an area of the ulna 24 which is relatively flat and substantially free of important ligaments and tendons. The upper or proximal end 36 of the ulnar brace member 12 includes a projection 39 (See FIG. 4), which is made up of a base 20, which is integral with the elongated portion 30, and a separate base cover 40, which secures to the base 20. The base 20 and base cover 40 together define a downwardly opening curved recess 41, which conforms to the shape of the ball 18 and receives the ball 18 with a close fit. The curved surface 38 in the base 20 defines half of the curved recess 41, and the curved surface 42 in the base cover 40 defines the other half of the curved recess 41. The cap 40 and base 20 terminate in vertical planar surfaces 35, 37, which abut each other when the cap 40 is secured to the base 20 by means of self-locking bolts 44 that extend through openings in the cap 40 and are anchored in threaded openings in the base 20. When the cap 40 and base 20 are secured together, the ball 18 at the upper end of the radial brace 16 is received in the downwardly opening curved recess 41 and is free to swivel and slide within that recess 41, in order to support the radius 22 relative to the ulna 24.

As shown clearly in FIG. 2, the ulnar brace member-12 is shaped so that, when it is mounted on the ulna 24, its upwardly opening recess 28 receives and is guided by the capitellum 34 of the humerus 26, and its downwardly opening recess 41 receives and guides the ball 18 of the radial brace 16 while permitting normal interaction between the natural trochlea 23 of the humerus 26 and the natural trochlear notch 25 of the ulna 24. As shown best in FIGS. 2 and 4, the elongated portion 30 of the ulnar brace member 12 conforms to the shape of the rear surface portion 29 of the ulna 24 below the proximal radial notch 27, and the screws 14 tighten the elongated portion 30 of the ulnar brace member 12 against that rear surface portion 29 of the ulna 24. The ulnar brace member 12 also defines an elongated vertical recess 31, which is received by the rear edge of the proximal radial notch 27, and the projection 39 has a curved outer surface portion 51 that fits into and conforms to the shape of the proximal radial notch 27 of the ulna 24. The downwardly-extending elongated portion 30 is on one side of the vertical recess 31, and the projection 39 with the downwardly opening recess 41 is on the other side of the recess 31. By fitting the projection 39 into the proximal radial notch 27 and by generally conforming to the shape of the outer surface of the ulna, the ulnar brace member 12 can be mounted on the proximal end of the ulna 24; while leaving the proximal end of the ulna 24 intact, and with the downwardly opening recess 41 positioned to receive the proximal end of the radius and the upwardly opening recess 28 positioned to receive the capitellum 34.

Once assembled, the base 20 and cover 40 also define a shallow, upwardly opening curved recess 28 at the upper or proximal end of the ulnar brace member 12. This upwardly opening recess 28 is axially aligned with the downwardly opening recess 41, and it has a rounded or curved shape which conforms to the shape of and receives the capitellum 34. The capitellum 34 is the rounded protuberance at the distal (or lower) end of the humerus that articulates with the radius 22. The recess 28 acts not only to receive the capitellum 34, but to mechanically cradle the capitellum 34 to keep it (and the humerus) in alignment with the prosthesis 10.

Looking in more detail at the radial brace 16, at the proximal end of the radial stem rod 46 are a flange 49 and a tear-shaped projection 50 axially aligned with the longitudinal axis of the radial stem rod 46. The tear-shaped projection 50 is received in a corresponding tear-shaped cavity 52 in the hemispherical ball 18 with a snap-fit, and the flat bottom surface 53 of the ball 18 abuts the top surface of the flange 49.

As indicated above, the ball 18 is able to pivotably rotate and slide within the downwardly opening recess 41 formed by the base 20 and the base cover 40. Since the ball 18 of the radial brace 16 is received in the downwardly opening recess 41 of the ulnar brace 12, and the capitellum 34 of the humerus 26 is received in the upwardly opening recess 28 of the ulnar brace 12, the radius 22 is thereby stabilized relative to the ulna 24 and relative to the humerus 26.

In this particular embodiment 10, the metal components of the prosthesis 10 are made from cobalt chromium. These metal components include the brace members 12 and 16, including the base 20 and base cover 40, the securing screws 14 and bolts 44, and the flange 49 and tear-shaped projection 50 on the brace member 16. The non-metal components are made from an ultra-high molecular weight polymer, such as UHMW polyethylene. These non-metal components include the ball 18.

To assemble and install the proximal radioulnar joint prosthesis 10, first the damaged portion of the proximal head of the radius bone 22 is excised and readied for receipt of the radial brace member 16. The radial stem rod 46 of the radial brace member 16 is pressed into the medullary cavity of the radius 22. The radial stem rod 46 may be cemented or adhered in place, if desired. Then the ball 18 is snapped onto the tear-shaped projection 50 to assemble the ball 18 onto the radial brace 16. Since the ball 18 is not initially mounted to the stem 46, a tool (not shown) may be used, acting against the flange 49 or against the projection 50, to "hammer" the stem rod 46 into the medullary cavity 48 of the radius 22 prior to snapping the ball 18 onto the projection 50. Then holes are drilled into the ulna bone 24 using a template to align the holes with the openings 32 in the ulnar brace member 12, and the ulnar brace member 12 is mounted, via self-locking screws 14, onto the upper portion of the ulna 24, as shown, with the elongated portion 30 of the ulnar brace member 12 in contact with the ulna 24.

As is best appreciated in FIGS. 3 and 4, the elongated portion 30 of the ulnar brace member 12 extends downwardly and tangentially from the base 20. This orientation allows the mounting of the elongated portion 30 onto a relatively flat area of the proximal ulna 24, where no important ligaments or muscle connections are located, while the downwardly opening recess 41 is axially aligned with the radius 22 and the upwardly opening recess 28 is axially aligned with the capitellum 34 of the humerus 26.

With the base cover 40 removed, the radius 22 is moved towards the ulna 24 until the ball 18 of the radial brace member 16 is inserted into the partial cavity 38 of the base 20. The base cover 40 is then installed onto the base 20 with the screws 44 so as to "capture" the ball 18 within the downwardly opening recess 41. The ball 18 (and therefore the radius 22) is able to rotate and slide within the cavity 42, which is fixed relative to the ulna 24. This stabilizes the radius 22 relative to the ulna 24, since the ligaments retain the ball 18 within the downwardly opening recess 41. The overall length of the radius 22, together with the radial brace member 16, is such that the ball 18 is trapped within the recess 41, and it is unlikely to "pop" out or otherwise become dislocated as the radius 22 rotates relative to the ulna 24 and as the elbow joint is flexed. The upwardly opening curved recess 28 receives the capitellum 34 of the distal humerus 26, as explained earlier. There generally is a slight space or gap between the capitellum 34 and the recess 28, so they do not come into contact until the person bears weight, at which point the capitellum 34 comes into contact with the recess 28, thereby providing support for the weight.

While the embodiment described above shows a simple means for rotationally securing the ball 18 of the radial brace member 16 to the ulnar brace member 12, various other mounting mechanisms could be used to achieve this result. For instance, the entire projection 39 containing the downwardly opening recess 41 could hinge up or out of the way far enough for the ball 18 to clear the edge of the recess and then could hinge downwardly and be fixed in the downward position to retain the ball 18 in the recess 41. Alternatively, the body that forms the downwardly opening recess and upwardly opening recess could be a separate piece from the ulnar brace member 12, designed to be placed over the ball 18 and then to be fixed relative to the ulnar brace member 12 by means such as snapping or bolting. Similarly, the ulnar brace member 12 could be secured to the ulna 24 by other means, such as by a shaft received in the cavity of the ulna 24 or by being adhered to the ulna 24.

While a few examples have been described above, it will be obvious to those skilled in the art that various modifications may be made to the embodiments described above without departing from the scope of the present invention as claimed.

What is claimed is:

1. A proximal radioulnar joint prosthesis, comprising:
  a radial brace member including a rod defining a longitudinal axis and distal and proximal ends; and a ball at the proximal end of said rod;
  an ulnar brace member having an upper end and a lower end and including
    a downwardly-extending elongated portion defining an elongated abutment surface shaped to abut and conform to the outer surface of the human ulna bone near its proximal end;
    a projection from said downwardly-extending elongated portion defining a downwardly opening curved recess including means for receiving and supporting said ball for rotation; and
    means for mounting said ulnar brace member on a human ulna near the proximal end of the ulna so as to place the projection that defines the downwardly opening curved recess in the proximal radial notch of the human ulna while leaving the proximal ulna intact.

2. A proximal radioulnar joint prosthesis as recited in claim 1, wherein said ulnar brace member projection includes a base portion and a separate cover, and means for securing said cover to said base, wherein said base and said cover together define said downwardly opening curved recess when said cover is secured to said base.

3. A proximal radioulnar joint prosthesis as recited in claim 2, wherein said ulnar brace member projection further defines an upwardly opening curved recess above said downwardly opening curved recess, said upwardly opening curved recess including means for receiving and being guided by the natural human capitellum.

4. A proximal radioulnar joint prosthesis as recited in claim 3, wherein said ball is releasably secured to said rod.

5. A proximal radioulnar joint prosthesis as recited in claim 4, wherein said elongated portion extends tangentially and downwardly from said projection, and wherein said ulnar brace member defines an elongated vertical recess between the projection and the elongated portion.

6. A proximal radioulnar joint prosthesis for mounting to the humerus, radius, and ulna bones of a patient, comprising:

a radial brace member, including an upwardly-projecting ball and means for mounting said radial brace member on the proximal end of a human radius; and an ulnar brace member including a projection defining a downwardly opening curved recess which includes means for receiving and rotationally supporting said ball; said projection including a base portion having a curved outer surface portion adapted to be received in the proximal radial notch and including at least one part that is separate from the base portion and that, when secured to the base portion, provides at least a portion of the downwardly opening curved recess; and including means for fixing said at least one separate part to said base portion;

said ulnar brace member also including a downwardly extending elongated portion which extends downwardly from said base portion and includes mounting means for mounting said ulnar brace member on an ulna, wherein said ulnar brace member defines an elongated vertical recess between said projection and said downwardly elongated portion, said recess being shaped to receive the front and rear edges of the proximal radial notch.

7. A proximal radioulnar joint prosthesis as recited in claim 6, wherein said ulnar brace member further defines an upwardly opening curved recess above said downwardly opening curved recess, wherein said upwardly opening curved recess includes means for receiving and being guided by the natural capitellum portion of the humerus.

8. A proximal radioulnar joint prosthesis as recited in claim 1, wherein the projection which defines the downwardly opening curved recess has an outer surface that conforms to the shape of the proximal radial notch of the human ulna.

* * * * *